(12) United States Patent
Vanmoor

(10) Patent No.: US 6,384,078 B1
(45) Date of Patent: May 7, 2002

(54) METHOD OF TREATING ELEVATED CHOLESTEROL LEVELS BY ENHANCING THE EFFECTIVENESS OF THE HUMAN IMMUNE SYSTEM

(76) Inventor: Arthur Vanmoor, 22 SE. 4 St., Boca Raton, FL (US) 33432-6016

(*) Notice: Subject to any disclaimer, the term of this patent is extended or adjusted under 35 U.S.C. 154(b) by 0 days.

(21) Appl. No.: 09/717,661

(22) Filed: Nov. 21, 2000

(51) Int. Cl.$^7$ .................. A61K 31/195; A61K 31/1425
(52) U.S. Cl. ....................................... 514/562; 514/369
(58) Field of Search .................................. 514/562, 369

(56) References Cited

U.S. PATENT DOCUMENTS

| | | | | |
|---|---|---|---|---|
| 3,892,852 A | * | 7/1975 | Joullie et al. | 424/180 |
| 3,950,387 A | * | 4/1976 | Joullie et al. | 260/468 |
| 5,032,608 A | * | 7/1991 | Dudrick | 514/396 |
| 5,272,166 A | * | 12/1993 | Breslow et al. | 514/390 |

OTHER PUBLICATIONS

"Effects of dietary methionine, cystine, and glycine endogenous hypercholesterolemia in hepatoma–bearing rats", Yagasaki, et al., J. Nutr. Sci. Viaminol., 1986, 32(6), 643–51.*

"Taurine enhances low density lipprotein binding internalization, and degradation by culture Hep G2 cells", Stephan et al., 1987, 262(13), 6069–73, abstract.*

* cited by examiner

Primary Examiner—Zohreh Fay
Assistant Examiner—Brian-Yong Kwon

(57) ABSTRACT

There is disclosed a method of treating elevated blood levels of cholesterol in a person in need of such treatment, which comprises enhancing the effectiveness of the person's immune system by the administration to such person of at least one aliphatic sulfur compound, preferably a sulfur-containing amino-acid derivative having the formula (I)

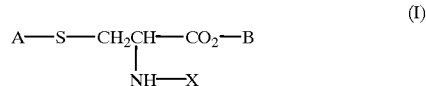

in which A is hydrogen or a carboxymethylene —$CH_2CO_2H$ group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

17 Claims, No Drawings

METHOD OF TREATING ELEVATED CHOLESTEROL LEVELS BY ENHANCING THE EFFECTIVENESS OF THE HUMAN IMMUNE SYSTEM

BACKGROUND OF THE INVENTION

1. Field of the Invention

This invention relates to a method of treating a person suffering from ill effects of elevated blood levels of cholesterol with an agent that enhances the effectiveness of the human immune system to mitigate and where possible eliminate the after-effects of elevated blood cholesterol levels.

2. Description of Related Art

The human immune system functions to maintain human individuality by fighting off foreign entities. The MERCK MANUAL, 16th edition, published 1992, at pages 279 to 303, which portion is here incorporated by reference, contains a detailed description of the parts of the immune system and of immunodeficiency diseases and hypersensitivity disorders to which it is subject. A table at pages 284–5 titled "Cytokines" lists the major effects of such cytokines or immunoeffective polypeptides as interleukin types, interferon types, alpha- and beta-tumor necrosis factor, three types of colony-stimulating factor, and alpha- and beta-transforming growth factor. Nothing in this publication relates to a metabolic disorder such as the excessive accumulation of cholesterol.

As is well known, cholesterol is a natural product found in many foods and is both synthesized and metabolized in the body. In some persons, metabolism of cholesterol is not able to keep pace with its intake and synthesis, so that cholesterol accumulates in the body. This constitutes a problem when such accumulation reaches the point that crystals of cholesterol deposit along the walls of blood vessels and there cause obstructions. The principal remedy for this condition is to limit intake of cholesterol. Certain organic compounds are somewhat effective in controlling blood levels of cholesterol. None of these, however, are without deleterious side effects However, the search by scientific techniques for better remedies for this as well as other suffering conditions is enormously costly. For economic reasons, moreover, the search tends to be skewed in the direction of finding novel remedies proprietary to their discoverers and owners. Novel remedies, of course, come into being with nothing known about either their safety or their effectiveness, so that both of these essential attributes need to be exhaustively studied before they can be used as intended.

In contrast, the art has tended to neglect the exploration of therapeutic properties of known substances that humans have been safely ingesting for untold generations. Along these lines, the present inventor has been able to bring about in susceptible individuals within a limited and reproducible time the appearance of headache, elevated blood pressure, facial pimples, signs of the so-called common cold, and pains in a joint by administering selected foods, food ingredients, and relatively harmless household chemicals as trigger substances, and to use these as research tools to study the effectiveness of certain nutrient substances in relieving these artificially produced conditions as well as their natural counterparts. As a result, certain water soluble amino carboxylic acid compounds are disclosed in U.S. Pat. No. 5,616,617 as effective against facial pimples; certain water soluble amino carboxylic acid compounds are disclosed in U.S. Pat. No. 5,626,831 as effective against the common cold; certain water soluble amino carboxylic acid compounds are disclosed in U.S. Pat. No. 5,707,967 as effective against headache; certain water soluble amino carboxylic acid compounds are disclosed in U.S. Pat. No. 5,708,029 as effective against elevated blood pressure, and certain water soluble amino carboxylic acid compounds are disclosed in U.S. Pat. No. 5,767,157 as effective against pain in a joint.

SUMMARY OF THE INVENTION

In accordance with this invention, there is provided a method of treating ill effects of elevated blood levels of cholesterol in a person in need of such treatment, which comprises the administration to such person of at least one aliphatic sulfur compound. The observed effect is believed to accompany enhancement of the effectiveness of the person's immune system.

The aliphatic sulfur compound preferably includes a sulfur-methylene moiety such as

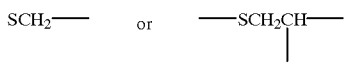

More preferably, the aliphatic sulfur compound also includes a carboxyl group, as in

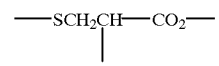

Still more preferably, the aliphatic sulfur compound is a sulfur-containing amino-acid derivative of an ethyl sulfide having the formula (I)

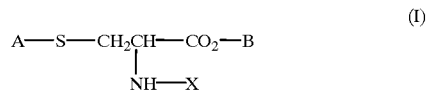

in which A is hydrogen or a carboxymethylene —CH$_2$CO$_2$H group, B is hydrogen or an alkyl group having 1 to 3 carbon atoms, and X is hydrogen, or an acyl group —CO—R in which R is an alkyl group having 1 to 3 carbon atoms, or a pharmaceutically acceptable salt of such compound.

In this compound, the ethyl sulfide group

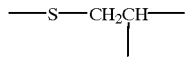

is believed to be responsible for the beneficial activity observed while the attached groups A, —NHX, and —CO$_2$B assist in delivering the compound to the site within the human organism where the beneficial activity is exerted.

In one preferred embodiment, A is hydrogen.

In a further preferred embodiment, A, B, and X are not simultaneously hydrogen.

Particularly suitable illustrative derivatives having the formula given above are tabulated by showing the assignments of A, B, and X in the above formula:

| Compound | A | B | X |
|---|---|---|---|
| 1 | —CH₂CO₂H | H | H |
| 2 | H | Y | COCH₃ |
| 3 | H | CH₃ | H.HCl |
| 4 | H | C₂H₅ | H.HCl |
| 5 | H | H | H |
| 6 | H | Y | H.HCl |

The present invention is based on the recognition that enhancing the effectiveness of the immune system in a person can be beneficial in augmenting the person's innate ability to resist the accumulation and deposition of excess cholesterol as well as the potentially dangerous effects thereof Consequently, the quality of life is improved.

In increasing the effectiveness of the human immune system according to this invention, mega-nutrient doses of 2 to 20 grams of a compound or compounds of formula (I) can be administered to a person with elevated blood levels of cholesterol one or more times daily, and continued until such levels are seen to diminish. Such doses can also be administered in a preventive manner to enhance the organisms ability to metabolize cholesterol and prevent its accumulation and deposition. Doses can be administered in any convenient manner, as by oral administration in any of the usual dosage forms, such as tablets, capsules, solutions, and dispersions in liquid foods such as soups and fruit juices. Alternatively, there can be given sterile solutions by direct injection into the bloodstream of the person to be treated, as well as by rectal suppositories.

EXAMPLE 1

Four male volunteers took 20 grams of a composition of several compounds of formula I daily for 6 weeks and observed 40% reduction of blood cholesterol levels.

What is claimed is:

1. A method of treating an elevated blood LDL cholesterol level in a person in need of such treatment, which comprises the administration to such person in the absence of a therapeutically effective amount of conventional LDL cholesterol lowering agent of at least one amino-acid derivative having the formula (I)

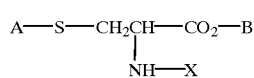

(I)

in which A is hydrogen or a carboxymethylene —CH₂CO₂H group, B is hydrogen or an alkyl group having 1 to 3 carbon atoms, and X is or an acyl group —CO—R in which R is an alkyl group having 1 to 3 carbon atoms, or a pharmaceutically acceptable salt of such compound.

2. The method of claim 1, wherein said amino-acid derivative is administered orally when elevated blood levels of cholesterol are observed.

3. The method of claim 1, wherein said amino-acid derivative is administered orally prior to or simultaneously with consumption of dietary cholesterol.

4. The method of claim 1, wherein said amino-acid derivative is administered in one to eight daily doses of 2 to 20 grams each.

5. The method of claim 1, wherein the total of said amino-acid derivative administered daily is in the range of 10 to 80 grams.

6. The method of claim 1, wherein said amino-acid derivative is the compound of formula (I) in which A is —CH₂CO₂H, B is H, and X is H.

7. The method of claim 1, wherein said amino-acid derivative is the compound of formula (I) in which A is H, B is H, and X is COCH₃.

8. The method of claim 1, wherein said amino-acid derivative is the compound of formula (I) in which A is H, B is CH₃, and X is H.HCl.

9. The method of claim 1, wherein said amino-acid derivative is the compound of formula (I) in which A is H, B is C₂H₅, and X is H.HCl.

10. A method of treating an elevated blood LDL cholesterol level in a person in need of such treatment, which comprises enhancing the effectiveness of the person's immune system by the administration to such person in the absence of a therapeutically effective amount of conventional LDL cholesterol lowering agent of at least one amino-acid derivative having the formula (I)

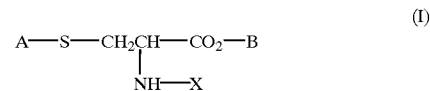

(I)

in which A is hydrogen or a carboxymethylene —CH₂CO₂H group, B is hydrogen or an alkyl group having 1 to 3 carbon atoms, and X is or an acyl group —CO—R in which R is an alkyl group having 1 to 3 carbon atoms, or a pharmaceutically acceptable salt of such compound.

11. The method of claim 1, comprising the administration of a plurality of compounds having formula (I).

12. The method of claim 10, comprising the administration of a plurality of compounds having formula (I).

13. The method of claim 10, wherein said amino-acid derivative is administered orally when elevated blood levels of cholesterol are observed.

14. The method of claim 10, wherein said amino-acid derivative is administered orally prior to or simultaneously with consumption of dietary cholesterol.

15. The method of claim 10, wherein said amino-acid derivative is administered in one to eight daily doses of 2 to 20 grams each.

16. The method of claim 10, wherein the total of said amino-acid derivative administered daily is in the range of 10 to 80 grams.

17. The method of claim 10, wherein said amino-acid derivative is the compound of formula (I) in which A is H, B is H, and X is COCH₃.

* * * * *